United States Patent [19]

Bron

[11] 4,343,305
[45] Aug. 10, 1982

[54] ADJUSTABLE-RATE, CONSTANT OUTPUT INFUSION SET

[76] Inventor: Dan Bron, 36 Palmach St., Haifa, Israel

[21] Appl. No.: 156,781

[22] Filed: Jun. 5, 1980

Related U.S. Application Data

[63] Continuation-in-part of Ser. No. 842,168, Oct. 14, 1977.

[51] Int. Cl.³ .............................................. A61M 5/00
[52] U.S. Cl. ............................. 128/214 R; 128/214 C; 137/501
[58] Field of Search ............... 128/214, 214 C, 214 D, 128/214 E, 214 F, DIG. 12, 214.2, 227; 137/501, 504

[56] References Cited

U.S. PATENT DOCUMENTS

| 172,163 | 1/1876 | Peebles | 137/501 |
|---|---|---|---|
| 611,519 | 9/1898 | Simmance | 137/501 |
| 2,219,408 | 10/1940 | Benz et al. | 137/501 |
| 3,357,448 | 12/1967 | Martin | 137/501 |
| 3,812,876 | 5/1974 | Krieter | 137/501 |
| 3,886,968 | 6/1975 | Murrell | 137/501 |
| 4,043,332 | 8/1977 | Metcalf | 128/214 E |
| 4,078,563 | 3/1978 | Tuseth | 128/214 C |
| 4,142,523 | 3/1979 | Stegeman | 128/214 C X |
| 4,142,524 | 3/1979 | Jassauaua et al. | 128/214 F |

Primary Examiner—Stephen C. Pellegrino
Attorney, Agent, or Firm—Lane, Aitken, Kice & Kananen

[57] ABSTRACT

There is provided an adjustable-rate, constant output infusion set connectable in-line in an intravascular infusion system. The infusion set comprises a connector piece connectable to a container for the infusion liquid and a head piece rotatably attached to the connector piece and connectable at its lower end to a tube leading to the infusion recipient. An elastically stretchable diaphragm is interposed between the connector piece and the head piece. The connector piece forms with the diaphragm a first chamber in direct communication with the container via an inlet port, and the head piece forms with the diaphragm a second chamber in direct communication with the recipient via a control port. The head piece is rotatably attachable to the connector piece for adjusting the flow rate therethrough. The set further comprises an annular member interposed between the connector piece and the head piece, and a passageway which connects the first chamber and the second chamber. The diaphragm by virtue of its elasticity maintains a constant pressure drop between the chambers, so that liquid passes the control port at a constant rate of flow, in spite of variations of liquid pressure in the ports.

20 Claims, 11 Drawing Figures

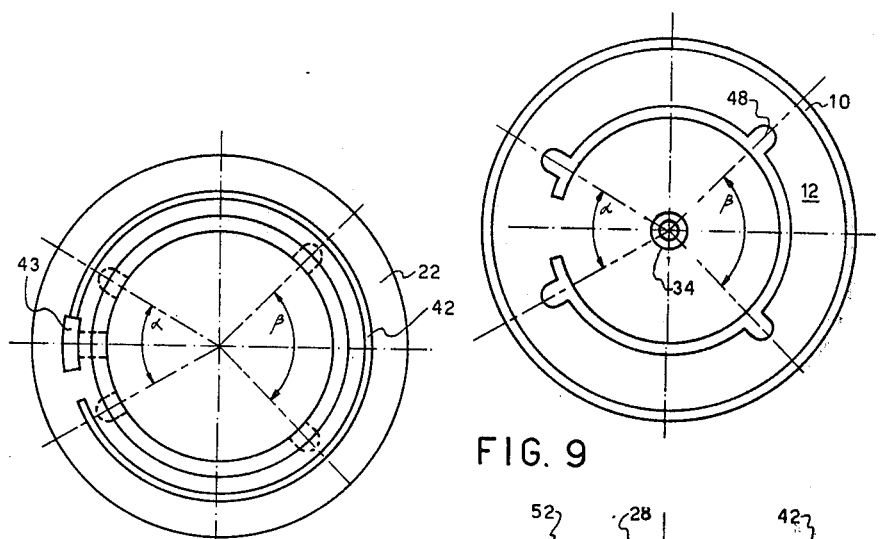
FIG. 9
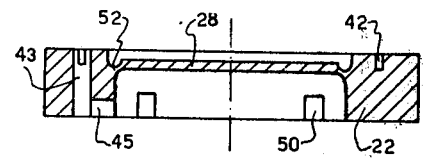
FIG. 10
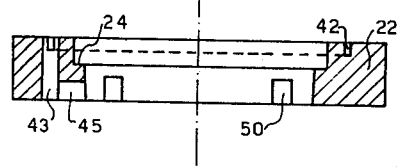
FIG. 7
FIG. 8
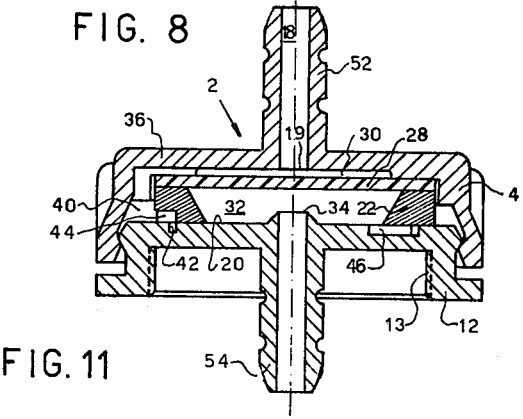
FIG. 11

ADJUSTABLE-RATE, CONSTANT OUTPUT INFUSION SET

This application is a continuation-in-part of prior application Ser. No. 842,168 filed on Oct. 14, 1977.

The present invention relates to an adjustable-rate, constant output infusion set, that is, to an infusion set adjustable to a wide range of flow or dripping rates and, once adjusted to a certain rate, maintains that rate through-out the entire infusion period.

Infusion, or more precisely, intravenous infusion is today a standard procedure both as emergency treatment for loss of blood, shock, dehydration, etc., and as therapeutic routine in a great many conditions requiring the slow infusion of various liquids also other than whole blood, plasma and saline. Whatever liquid is used, is gravity-fed into the patient's venous system over periods of time that may extend over hours and even days.

Of particular importance for the efficacy of the infusion treatment is a steady dripping rate, yet it is precisely in this point that the standard infusion set fails: within the first two hours, there is a dripping-rate falloff of almost 25%. While this is to a great extent due to the flow-control clamp, there are also other causes such as variations of the fluid level in the container with respect to the position of the patient, variations in the venous pressure of the latter, and partial clogging of the hypodermic needle or cannular used. This obliges the medical staff to spend additional time monitoring and readjusting the infusion set, and even so, the use of the standard infusion set is liable to result in a non-uniform and sometimes improper dripping rate.

It is one of the objects of the present invention to overcome these and other drawbacks and difficulties of the prior art, and to provide an inexpensive infusion set with an adjustable, constant flow or dripping rate independent of the difference in height between the liquid level in the container and the patient, or of the venous pressure of the patient.

This the invention achieves by providing an adjustable-rate, constant output infusion set connectable in-line in an intravascular infusion system, comprising a connector piece connectable to a container for the infusion liquid and a head piece rotatably attached to said connector piece and connectable at its lower end to a tube leading to the infusion recipient, said connector piece and head piece defining a space delimited by an internal bottom of said connector piece and an internal top surface of said head piece, an elastically stretchable diaphragm interposed between the internal bottom of said connector piece and the top surface of said head piece, said connector piece forming with the diaphragm a first chamber in direct communication with said container via an inlet port, and said head piece forming with said diaphragm a second chamber in direct communication with said recipient via a control port, said head piece being rotatably attachable to said connector piece for permitting relative rotation of said head piece and said connector piece for adjusting the flow rate therethrough and said set further comprising an annular member interposed between said connector piece and said head piece, and at least one passageway the dimensions of which remain unchanged during operation and which connects said first chamber and said second chamber, wherein upon being exposed to a liquid pressure differential between said first chamber and said second chamber, said diaphragm, solely by virtue of its elasticity, is elastically stretchable and, at least a portion thereof, movable between positions closer to said control port to thereby reduce the rate of flow therethrough and positions further away from said control port, to thereby increase the flow therethrough, said diaphragm maintaining a constant pressure drop between said chambers, whereby said liquid passes said control port at a constant rate of flow, in spite of variations of liquid pressure in at least one of said ports.

With specific reference now to the figures in detail it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 7 and 8 are an enlarged top view and a cross-sectional view, respectively, of the annular member of the embodiment shown in FIG. 6;

FIG. 9 is an enlarged top view of the head piece of the embodiment of FIG. 6;

FIG. 10 is a cross-sectional view of a diaphragm integral with the anular member of the embodiment of FIG. 6, and FIG. 11 is a cross-sectional view of another embodiment of the device according to the invention.

Figure 1:
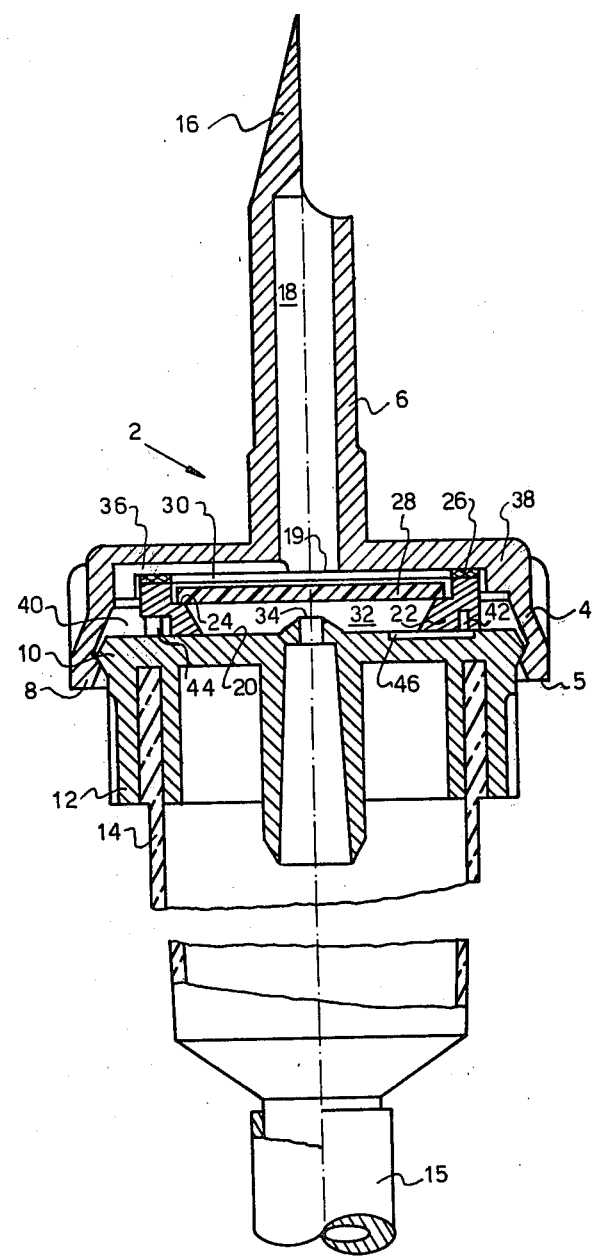
FIG. 1 is an enlarged partial cross section of a first embodiment of the infusion set according to the invention.

There is shown in FIG. 1 a connector piece 2 comprising a coupling portion 4 and a snout portion 6. With the aid of an internal beading 8, the coupling portion 4 snap-locks onto an appropriately dimensioned and shaped external beading 10 of a head piece 12, to which is attached an at least partly transparent drip chamber 14, to whose lower end there is connected a flexible tube 15 leading to the IV hypodermic needle or cannula.

The snout portion 6 has a pointed end 16, part of which is cut away along an axial plane, thereby exposing the upper end of the inlet duct 18, the lower end of which, constituting an inlet port 19, leads into the coupling portion 4. With this sharp, pointed end 16, the snout 6 can be forcibly pushed into the sealed end of the infusion-fluid container or bottle (not shown), thereby establishing a fluid connection between the bottle and the infusion set.

In the space defined by the inside of the connector piece 2 and the top face 20 of the head piece 12, there is mounted an annular member 22 having an internal, step-like recess 24 and made of a rigid, substantially non-deformable material. Located between the top surface of the annular member 22 and the inside bottom of the coupling portion 4, there is seated a ring 26 made of an elastomer. The thickness of this ring 26 is such that, when the latter is mounted on the annular member 22, the internal beading 8 of the coupling portion 4 will not snap over, and lock onto, the external beading 10 of the head piece 12, until the ring 26 is slightly flattened by a manually applied compressive force which, aided by the slanting faces of the respective beadings 8 and 10 also causes the edge portion 5 of the coupling portion 4 to spread enough to permit the beading 10 to slip over the beading 8 and, thus, to establish the snap lock. At the same time, the restoring force exerted by the now elastically deformed ring 26 provides the stress required to maintain an intimate, liquid-tight contact between the two beadings 8 and 10, while yet permitting a relative rotational movement between the two, for a purpose to be explained below.

Freely seated in the recess 24 of the annular member 22 is a diaphragm 28, made of an elastically stretchable material and forming with the connector piece 2 a first chamber 30 in direct communication with the infusion-liquid container via the inlet duct 18, as well as forming a second chamber 32 with the head piece 12 in direct communication with the drip chamber 14 via a raised control port 34.

Figure 2:
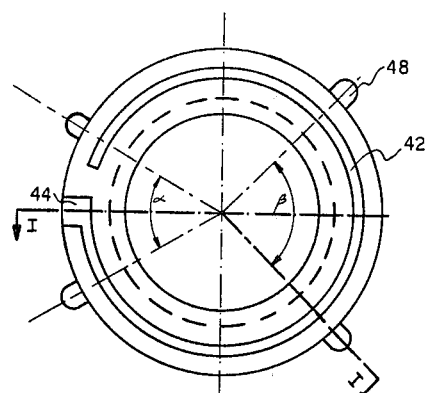
FIG. 2 is a bottom view, also enlarged, of the annular member of the embodiment shown in FIG. 1.
Figure 3:
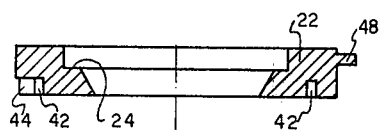
FIG. 3 is an enlarged cross section, along planes I—I in FIG. 2, of the annular member.

While as inferable from the above, the diaphragm 28 intervenes, and prevents direct communication between, the first chamber 30 and the second chamber 32, provision must obviously be made for the infusion fluid to reach the port 34. This is accomplished by establishing a passage way between the first chamber 30 and the second chamber 32, which bypasses the diaphragm 28 and the dimensions of which remain unchanged during operation. The first section of this passage way consists of a channel 36 provided in the bottom of the coupling portion 4 and continued also in the centering rim 38 (see also FIG. 4), through which channel 36 the fluid, gravity-fed from the container, reaches an annular space 40 surrounding the member 22. The latter, shown to better advantage in FIGS. 2 and 3, is provided on its bottom face with a narrow circular groove 42 with an angular extent of somewhat less than 360°, as well as with a passage 44 facilitating access to the narrow groove 42 and establishing communication between the latter and the annular space 40. So far it has been shown how the infusion fluid can reach the narrow groove 42 via the channel 36, the annular space 40 and the passage 44. For the infusion fluid to reach the second chamber 32 and, thence, the drip chamber 14, yet another passage way is required, which is provided in the form of a wide groove 46 extending radially outward at least as far as to be with its full width below the narrow groove 42 and radially inward far enough to be fully open towards the second chamber 32, as clearly shown in FIG. 1.

The channel 36, the passage 44 and the wide groove 46 are all of an effective cross section large enough to easily accommodate flows of a magnitude characteristic of infusion devices, and cause only a relatively small pressure drop, indicated as a differential pressure on the surfaces of the diaphragm 28. The narrow, circular groove 42 on the other hand, having a typical cross section of 0.1 mm$^2$, constitutes a real flow restriction. As the infusion liquid makes its way from the first chamber 30 via the above described passage way into the second chamber 32 and the drip chamber 14, it encounters the flow resistance offered by the narrow groove 42, which causes a detectable pressure drop as a consequence of which the pressure in the second chamber 32 will be lower than that in chamber 30. Due to this pressure differential, the elastic diaphragm 28 will bulge downward and its central zone will approach the control port 34, restricting the outflow therethrough. A restricted outflow, on the other hand, will increase liquid pressure in the second chamber 32, thereby reducing the pressure differential between the two chambers and permitting the elastic forces of the diaphragm to reduce the bulge to some degree, thereby again increasing outflow. An equilibrium is eventually established, which is the working point of this flow-regulating device, which depends only on the elastic strength of the diaphragm. Any change in the dripping rate caused by extraneous agents is immediately corrected by a compensatory movement of the elastic diaphragm between positions closer to the control port 34, thereby reducing flow which for some reason has increased beyond the set-point, and positions further away from the control port 34, thereby increasing flow which for some reasons has fallen below the setpoint.

In the foregoing, a detailed explanation has been given concerning the mechanism by which a given dripping rate will remain constant in spite of variations in the container liquid level/patient distance, in the patient's venous pressure, or in spite of partial clogging of the IV-needle or cannular. In the following, a description will be given of the manner by which a desired dripping rate can be set.

Flow, that is, the dripping rate, is a function of the flow resistance offered by the restrictive section and the above-mentioned pressure drop. The latter being constant and solely depending on the elastic properties of the diaphragm, it follows that the dripping rate can be varied only by varying the flow resistance. This can be done by varying the effective or active length of the restrictive section constituted by the narrow groove 42 of the passage way.

In the infusion set according to this embodiment of the invention, the active length of this restrictive portion of the passage way can be varied. As the active length of the narrow groove 42 is the length of the arc-like groove section between the passage 44 (where the restrictive path begins) and the point in the groove section directly above the wide groove 46 (where the restrictive path ends, as the fluid is now free to pass into the relatively non-restrictive wide groove 46), rotating the annular member 22 in the clockwise sense relative to the wide groove 46 in the head piece 12 will shorten the active restrictive section, thereby increasing the dripping rate, while rotating this member 22 in the counterclockwise sense will lengthen the active restrictive section, thereby reducing the dripping rate.

As in the assembled state of the infusion set, the annular member 22 is of course inaccessible, its rotation for purpose of dripping-rate adjustment is effected by rotating the connector piece 2 relative to the head piece 12. To facilitate this action, the annular member 22 is provided with a number of protruding driving lugs 48 (see FIGS. 2 and 3) which, in the assembled state of the set, fit into appropriately shaped and spaced recesses 50 provided in the centering rim 38 of the connector piece 2 (see FIG. 4). Thus, by rotating the connector piece 2 relative to the head piece 12 (for which purpose both of these components are provided with gripping serrations or knurls), one also rotates the annular member 22 relative to the wide groove 46. A circumferential, arbitrary scale is conveniently provided on the connector piece 2, with an index mark provided on the head piece 12. The highest value on the scale is best marked by a special symbol, say the letter "P" for "Prime": when set to this position, the passage 44 in the annular member 22 will be located directly above the wide groove 46 on the top surface of the head piece 12, completely neutralizing the flow-restricting narrow groove 42. In this position, the infusion set can be rapidly "primed", i.e., filled with liquid, before infusion begins. Only after this priming operation is the infusion set adjusted to the desired dripping rate.

As, at a given setting, the dripping rates are also a function of the specific gravities and viscosities of the different infusion liquids, it is obvious that the dripping-rate scale cannot be an absolute scale. However, the same infusion liquid (allowing for small variations in specific gravity and viscosity due to inevitable variations in concentrations and temperatures) used at the same setting, will always result in the same dripping rates.

Figure 4:
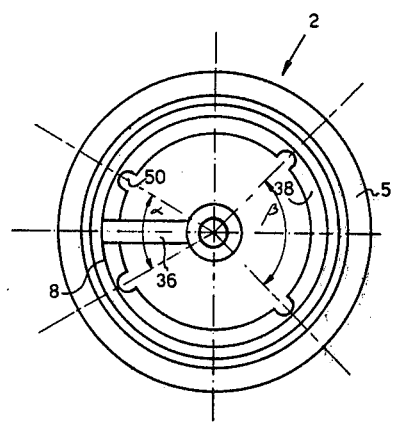
FIG. 4 is a bottom view of the connector piece of the embodiment of FIG. 1.

Returning to the driving lugs 48 of FIGS. 2 and 3, and the appropriate recesses 50 in FIG. 4, it should be noted that respective pairs of lugs and recesses are not spaced at the same angular distances ($\alpha \neq \beta$). This has the purpose of making it impossible to assemble the annular member 22 in more than one position, which would make the scale useless.

Figure 5:
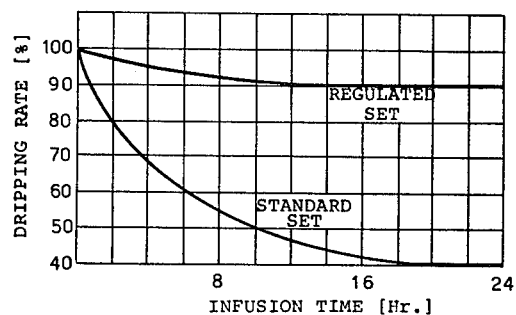
FIG. 5 is a graph indicating the relative dripping rate as a function of infusion time, both for the standard infusion set and for the set according to the invention.

FIG. 5 is a graph showing the relative dripping rate as a function of infusion time for both the standard infusion set and the set according to the invention. It is clearly seen that, while the dripping rate of the infusion set according to the invention settles down to a perfectly constant 90% of the initial rate after about 12 hrs, the standard-set dripping rate has not become fully constant even after 24 hrs, during which it has dropped to about 40% of the initial rate.

Figure 6:
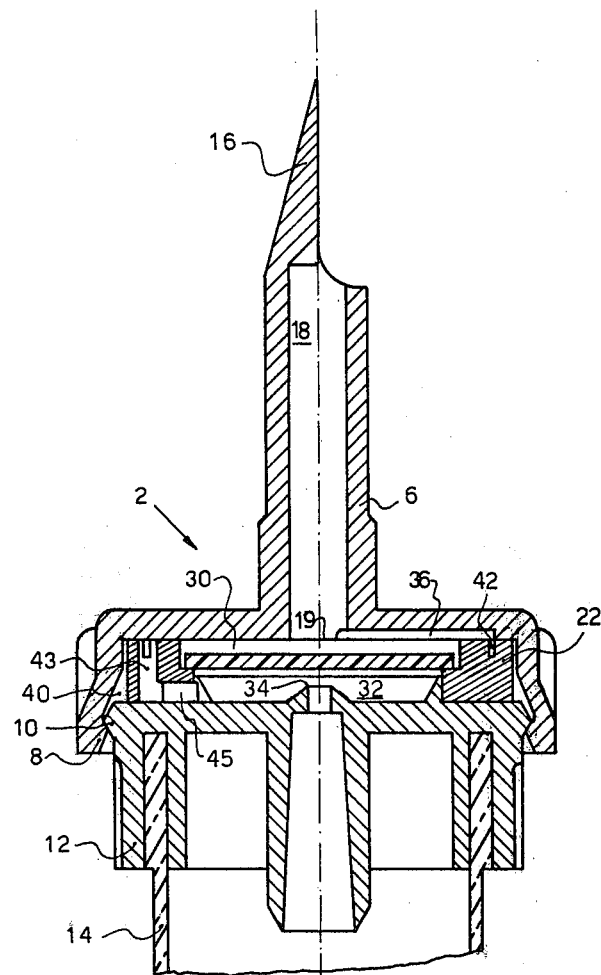
FIG. 6 shows an enlarged cross-sectional view of another embodiment of the present invention.

FIG. 6 is an enlarged cross-sectional view of another embodiment of the invention, which differs from the previous embodiment in that the elastically deformable ring 26 has been dispensed with, its stress-providing task having been taken over by the annular member 22 which is now made of an elastomer and is therefore elastically deformable itself. Another difference is the location of the narrow groove 42, which is now on the top surface of the annular member 22 (see FIGS. 7 and 8). The groove 42 passes into a duct 43 of a relatively large cross section which passes through the entire thickness of the member 22 and, via a passage 45, leads into the second chamber 32. As a consequence of these modifications, the annular member 22 must now be rotatable relative to the connector piece 2, and not, as before, relative to the head piece 12. This is achieved by making the drive lugs 48 now part of the top surface of the head piece (see FIG. 9) and providing the appropriate recesses 50 in the annular member 22 (see FIGS. 7 and 8). A substantial advantage of this embodiment is the fact that the infusion fluid has no access now to the annular space 40, thereby relieving the snap lock of its previous sealing function. Otherwise, the operational principles of these two embodiments are identical, as are the rest of their structural features.

A slightly modified version of the above embodiment has an elastic diaphragm 28 which is integral with the annular member 22 and is illustrated in FIG. 10. To maintain complete freedom of movement of the diaphragm 28, an annular groove 52 reduces the connection between the diaphragm and the body of the annular member 22 to a mere film just strong enough to withstand the full liquid pressure during the priming stage.

The clamp which, in standard infusion sets, is indispensible for dripping-rate regulation is used in the infusion set according to the invention only during the priming stage, and whenever infusion is to be interrupted.

It is seen in FIGS. 1 and 6 that, contrary to conventional design, the diaphragm 28 is not clamped to its carrier, in that case the annular member 22, but freely seated therein. It has been found that with diaphragms of this size, the free diameter of which is about 14 mm, and with the pressures involved in infusion sets, clamping could be dispensed with, without fear of direct fluid communication between the first and the second chamber. The absence of clamping has also a beneficial effect on the uniformity of the elastic properties of the diaphragms.

FIG. 11 is an "in-line" version of the infusion set according to the invention, which can be used without a drip chamber 14 and has no pointed snout 6, instead of which there are provided an inlet connector 52 and an outlet connector 54 for tubing. For uses requiring the provision of a drip chamber, connecting means for the attachment of such a chamber are provided, for example an internal thread 13 as shown. In contradistinction to the embodiments of FIGS. 1 and 6, the diaphragm 28 of the present embodiment is rigidly clamped between the bottom of the coupling portion 4 and the top face of the annular member 22 which latter, as in the embodiment of FIG. 1, is rotatable together with the coupling portion 4 relative to the head piece 12. A further difference between the previous embodiments and the embodiment of FIG. 11 is the location of the flow-restricting portion 42 of the passage way, which is here provided on the top face 20 of the head piece 12. The functions of the channel 36, the annular space 40, the passage 44 and the wide groove 46 are analogous to the functions of these details in the former embodiments, and so is the manner in which the dripping rate is set and maintained.

It should be understood that the flow-restriction portion or narrow groove 42 can also be provided in the bottom surface of the coupling portion 4, in which case the annular member obviously rotates together with the head piece 12 relative to the coupling portion 4.

While in the embodiments described, the flow-restrictive properties of the groove 42 are based on its small cross section, a similar restrictive effect could be obtained also by a groove of larger cross section, but greater length. Such a groove could be accommodated on the relatively small annular surface of the member 42 in the form, e.g., of a meander or other labyrinth device per se known.

As most infusion liquids today are stored and used in flexible plastic containers, no vacuum problem arises as the contents of these containers are slowly drained. Glass containers are still used, however, and require vacuum relief. For this purpose, the snout 6 of the connector piece 2 can be provided with an axial bore opening into the cut-away part of the pointed end 16, (FIG. 1) and communicating with the atmosphere at a point near the lower end of the snout 6. The "breather" opening thus provided is covered by a special filter which will permit air to enter the container, but will not allow the infusion liquid to leak through.

While particular embodiments of the invention have been described, it will be evident to those skilled in the art that the present invention may be embodied in other specific forms without departing from the essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are, therefore, intended to be embraced therein.

What is claimed is:

1. An adjustable-rate, constant-output infusion set comprising:
   an inverted-cup-shaped connector piece having substantially cylindrical walls and a downward-facing, bottom surface provided with an inlet port,
   a head piece rotatably engaging said connector piece;
   a member comprised at least by an annular portion, interposed between and rotatable relative to either of, said connector piece and said head piece, and having means rendering it stationary relative to the other one of said pieces;
   an elastically stretchable diaphragm at least the radial position of which is maintained by said member and which diaphragm defines with its upper surface a first chamber comprising said inlet port, and with its lower surface a second chamber comprising a control port, wherein, upon being exposed to a liquid pressure differential between said first chamber and said second chamber, at least a portion of said diaphragm, due to its elastic stretchability, is movable between positions closer to said control port to thereby reduce the rate of flow therethrough, and positions further away from said control port, to thereby increase the flow therethrough, to maintain a constant rate of flow, and further comprising
   means defining a passageway leading from said first chamber via said member into said second chamber, said passageway including at least one first portion in which flow is relatively unobstructed as well as at least one second portion in which flow is relatively restricted, the restrictive effect of which second portion determines said differential pressure and, thus, the flow rate of said infusion set, wherein said restrictive effect can be varied by means of a rotary displacement of one of said pieces relative to the other.

2. The infusion set as claimed in claim 1, wherein said second, flow-restricting portion is an arcuate groove.

3. The infusion set as claimed in claim 2, further comprising a connecting groove in an upward-facing surface of said head piece, connecting said arcuate groove to said second chamber, wherein said first portion of said passageway connects said first chamber around said diaphragm to a selectable point in said arcuate groove to maintain continuous flow of fluid to said arcuate groove, and wherein the length of said arcuate groove through which fluid passes is variable by rotating said member to vary the point at which said connecting groove intersects said arcuate groove.

4. The infusion set as claimed in claim 2, further comprising a connecting groove in said downward-facing surface of said connector piece connecting said first chamber to a selectable point on said arcuate groove, wherein said first portion of said passageway connects a fixed point of said arcuate groove to said second chamber, and wherein the length of said arcuate groove through which fluid passes is variable by rotating said member with respect to said connector to change the point of the intersection of said first passageway portion in said downward-facing surface with said arcuate groove.

5. The infusion set as claimed in claim 2, further comprising a connecting groove in the upward-facing surface of said head piece connecting said arcuate groove at a fixed point to said second chamber, means defining a passageway in the lower surface of said member, said passageway intersecting said arcuate groove, means connecting said passageway in said lower surface to said first chamber, wherein the length of said arcuate groove through which fluid passes is variable by rotating said member with respect to said head piece to change the point of intersection of the passageway in the lower surface of said member with said arcuate groove.

6. The infusion set as claimed in claim 1, wherein at least one of said connector piece or head piece is provided with connection means for connecting the same to tubing.

7. The infusion set as claimed in claim 1, wherein said head piece is provided with connecting means for attachment of a drip chamber.

8. The infusion set as claimed in claim 1, wherein said connector piece is provided with a snout for introducing at least its upper end into a fluid container.

9. The infusion set as claimed in claim 1, wherein said head piece is provided with means for the connection thereto of an at least partly transparent drip chamber.

10. The infusion set as claimed in claim 1, wherein said second, flow-restricting portion is located on the upward-facing surface of said member.

11. The infusion set as claimed in claim 1, wherein said second, flow-restricting portion is located in the downward-facing surface of said member.

12. The infusion set as claimed in claim 1, wherein said second, flow-restricting portion is located in the downward-facing surface of said connector piece.

13. The infusion set as claimed in claim 1, wherein said second, flow-restricting portion is located on the upward-facing face of said head piece.

14. The infusion set as claimed in claim 1, wherein said member is made of a rigid material.

15. The infusion set as claimed in claim 1, wherein said member is made of an elastomer.

16. The infusion set as claimed in claim 1, wherein said diaphragm is freely seated in said member.

17. The infusion set as claimed in claim 1, wherein said diaphragm is fixedly clamped to said member.

18. The infusion set as claimed in claim 1, wherein said diaphragm is an integral part of said member.

19. The infusion set as claimed in claim 1, wherein one of said pieces is provided with a peripheral scale and the other one with an index mark, to facilitate reproducibility of flow-rate settings.

20. The infusion set as claimed in claim 19, wherein said scale is provided with a special mark, whereby, when said index mark is set to said special mark, said second, flow-restricting portion of said passageway is neutralized.

* * * * *